(12) United States Patent
Mather et al.

(10) Patent No.: US 10,519,568 B2
(45) Date of Patent: Dec. 31, 2019

(54) OPTICALLY AND MECHANICALLY ACTIVE NANOSCALE MEDIA

(71) Applicants: Patrick T. Mather, Syracuse, NY (US); Amir Torbati, Jamesville, NY (US); Ryan Mather, Syracuse, NY (US)

(72) Inventors: Patrick T. Mather, Syracuse, NY (US); Amir Torbati, Jamesville, NY (US); Ryan Mather, Syracuse, NY (US)

(73) Assignee: Syracuse University, Syracuse ( * ) Notice: Subject to any disclaimer, the term of this patent is extended or adjusted under 35 U.S.C. 154(b) by 790 days.

(21) Appl. No.: 14/244,276

(22) Filed: Apr. 3, 2014

(65) Prior Publication Data

US 2014/0303490 A1    Oct. 9, 2014

Related U.S. Application Data

(60) Provisional application No. 61/808,344, filed on Apr. 4, 2013.

(51) Int. Cl.
*A61B 5/06* (2006.01)
*A61K 49/18* (2006.01)
*D01D 5/00* (2006.01)

(52) U.S. Cl.
CPC ............ *D01D 5/0038* (2013.01); *A61B 5/064* (2013.01)

(58) Field of Classification Search
None
See application file for complete search history.

(56) References Cited

U.S. PATENT DOCUMENTS

| | | | | |
|---|---|---|---|---|
| 8,921,473 B1* | 12/2014 | Hyman | ............... | C08K 3/04 423/445 R |
| 2009/0306226 A1* | 12/2009 | Suzarte Paz | ......... | A61K 9/2027 514/772.4 |
| 2011/0263037 A1* | 10/2011 | Herz | .................. | C08K 3/36 436/163 |
| 2014/0128345 A1* | 5/2014 | Woodrow | ............ | A61K 31/505 514/80 |
| 2015/0134051 A1* | 5/2015 | Donadio | .................. | A61F 2/064 623/2.4 |
| 2016/0041135 A1* | 2/2016 | Lannutti | ............ | G01N 21/6408 435/29 |

* cited by examiner

*Primary Examiner* — Patricia J Park
(74) *Attorney, Agent, or Firm* — Bond Schoeneck & King, PLLC; David Nocilly; George McGuire

(57) ABSTRACT

The present invention relates to a method for incorporating dye and/or nanoparticles into polymer films and into electrospun polymeric nanofibers, and, more specifically, to a method for electrospinning a molecularly homogenous solution of dye (and/or nanoparticles) and polymer dissolved in a mutual solvent leading to uniform distribution of dye across the cross-section of each constituent fiber and to resulting nanofibers with the dye/nanoparticles incorporated therein.

14 Claims, 12 Drawing Sheets

OPTICALLY AND MECHANICALLY ACTIVE NANOSCALE MEDIA

CROSS-REFERENCE TO RELATED APPLICATIONS

The present application claims priority to U.S. Provisional No. 61/808,344 filed on Apr. 4, 2013.

BACKGROUND OF THE INVENTION

1. Field of the Invention

The present invention relates to a method for incorporating dye and/or nanoparticles into polymer films and into electrospun polymeric nanofibers, and, more specifically, to a method for electrospinning a molecularly homogenous solution of dye (and/or nanoparticles) and polymer dissolved in a mutual solvent leading to uniform distribution of dye across the cross-section of each constituent fiber and to resulting nanofibers with the dye incorporated therein.

2. Description of the Related Art

The world market for neonatal and pediatric internal feeding devices in 2013 is $2.06 billion and is estimated to grow at the rate of 4.9% and reach $2.62 billion by 2018. The nasogastric (NG) tube market is generating the second largest revenue after enteral feeding pumps, accounting for 14% and 59% of the overall market respectively. Proper placement of NG tubes is critical to avoid perforation injuries and instillation of nutrient solution into lungs or body cavities. Currently radio-opaque markings are visualized radiologically to verify placement, as well as color pH sensors and ultrasound. A need exists for improved non-invasive real time imaging of pediatric NG tubes that avoids the use of ionizing radiation.

Electrospinning is a technique that is used for fabrication of nanofibers from thermoplastic, solvent-soluble polymers. Near Infrared (NIR) dyes function by absorbing light in the near IR portion of the optical spectrum and emitting light (in response to this) at a different wavelength also in the near IR portion of the optical spectrum. Near IR light is particularly interesting for medical applications, as mammalian tissue is particularly transmissive in this portion of the optical spectrum (just put a lamp behind your hand and you can see red light transmitted), indicating that it may be useful surgically.

Shape memory (SM) polymers are polymeric networks that feature a permanent, stress-free state and a multitude of temporary shapes fixed by mechanical manipulation in a rubbery state (above Tm or Tg, termed "triggering temperature"), followed by cooling. An environmental stimulus can be applied to trigger a shape transition from temporary to permanent shape. Highly entangled polymers can feature a shape memory, entanglements serving as physical crosslinks if their lifetime is longer than the deformation time. Currently, a method of incorporating a dye into polymer films and into electrospun polymeric nanofibers is accomplished by diffusion from an immersion solution.

BRIEF SUMMARY OF THE INVENTION

The present invention recognizes that there is a need for new ways to image implanted medical devices and surgical tools that avoids the use of harmful ionizing radiation, including x-ray imaging. Near infrared (NIR) fluorescence is a viable alternative owing to the relative transparency of human tissue to NIR light. Polymers containing nanoparticles and dyes are highly desired for a number of commercially and medically relevant applications, including high sensitive sensors, medical devices, and drug delivery. Incorporation of dyes and nanoparticles by diffusion is a method that has been widely used; however, this approach is problematic in that it lacks uniformity and control over the incorporation. For example, diffusion of dye into the fibers of an electrospun web will naturally lead to inhomogeneous concentration gradients from fiber surface to fiber core. This problem is further compounded in films due to the larger diffusion length scale of the film or coating thickness. Consequently, the release of nanoparticles or dyes from the polymer is neither uniform nor controllable. It is further desirable to incorporate dyes or nanoparticles with specific optical absorption and emission characteristics into thermoplastic polymer hosts in order to yield light-activated polymers that are easily imaged in a surgical scenario. For example, incorporating indocyanine green (ICG) dye, which has a near-infrared (NIR) excitation and emission wavelength (ICG absorbs mainly between 600 nm and 900 nm and emits fluorescence between 750 nm and 950 nm), into a polymeric medical device would allow that device to be easily detected for spatial location and using an NIR imaging system. No method is available to effectively incorporate NIR dyes into polymeric articles, a limitation an embodiment of the present invention addresses. No reports exist concerning the more direct process of electrospinning of thermoplastic polymers with the dye of choice by dissolving the dye in the polymer solution being electropun. The process by which dye is incorporated can have a significant difference on the distribution of dye in the material. Various embodiments of the present invention may be advantageous in that they may solve or reduce one or more of the potential problems and/or disadvantages discussed above.

Various embodiments of the present invention may exhibit one or more of the following objects, features and/or advantages:

It is therefore a principal object and advantage of the present invention to provide a method to uniformly incorporate dyes and/or nanoparticles into the thermoplastic polymers via electrospinning, and proposes its utility in imaging and actuation.

It is another object and advantage of the present invention to provide a method and product that allows for the imaging of an implanted medical device or surgical tool that avoids the use of harmful ionizing radiation, including x-ray imaging (e.g., by using NIR light instead of x-ray imaging to visualize objects beneath the skin).

It is a further object and advantage of the present invention to provide a method where a particular electrospun web can be heated (with or without dye or nanoparticle incorporation) so that the web shrinks, enabling use of the dye-incorporated fibers as a "shrink-wrap" film or band (indicating that electrospinning itself provides a means to fix a temporary shape of a particular SMP). One example implementation of this discovered phenomenon is the simple addition of NIR-fluorescent markers to such surgical and medical devices as catheters, guidewires, and feeding tubes.

In accordance with the following objects and advantages, an embodiment of the present invention provides a method including the step of electrospinning a molecularly homogeneous solution of dye and polymer dissolved in a mutual solvent, which can lead to uniform distribution of dye across the cross-section of each constituent fiber. In doing so, it was unexpectedly discovered that the fluorescence intensity of dye incorporated into nanofibers is dramatically higher than when incorporated in films of the same host polymer. This effect of an increase in intensity is important to the successful utilization of NIR-emitting materials in the imaging for medical devices and for other applications. Further, it was observed, unexpectedly, that the materials shrink dramatically upon heating. There are no limitations in incorporating thermally unstable dyes in this technique since the process can be conducted at room temperature.

The details of one or more embodiments are described below and in the accompanying drawings, including successful electrospinning of thermoplastic polymer (PVAc) containing (ICG) dye. Other objects and advantages of the present invention will in part be obvious, and in part appear hereinafter.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 3:
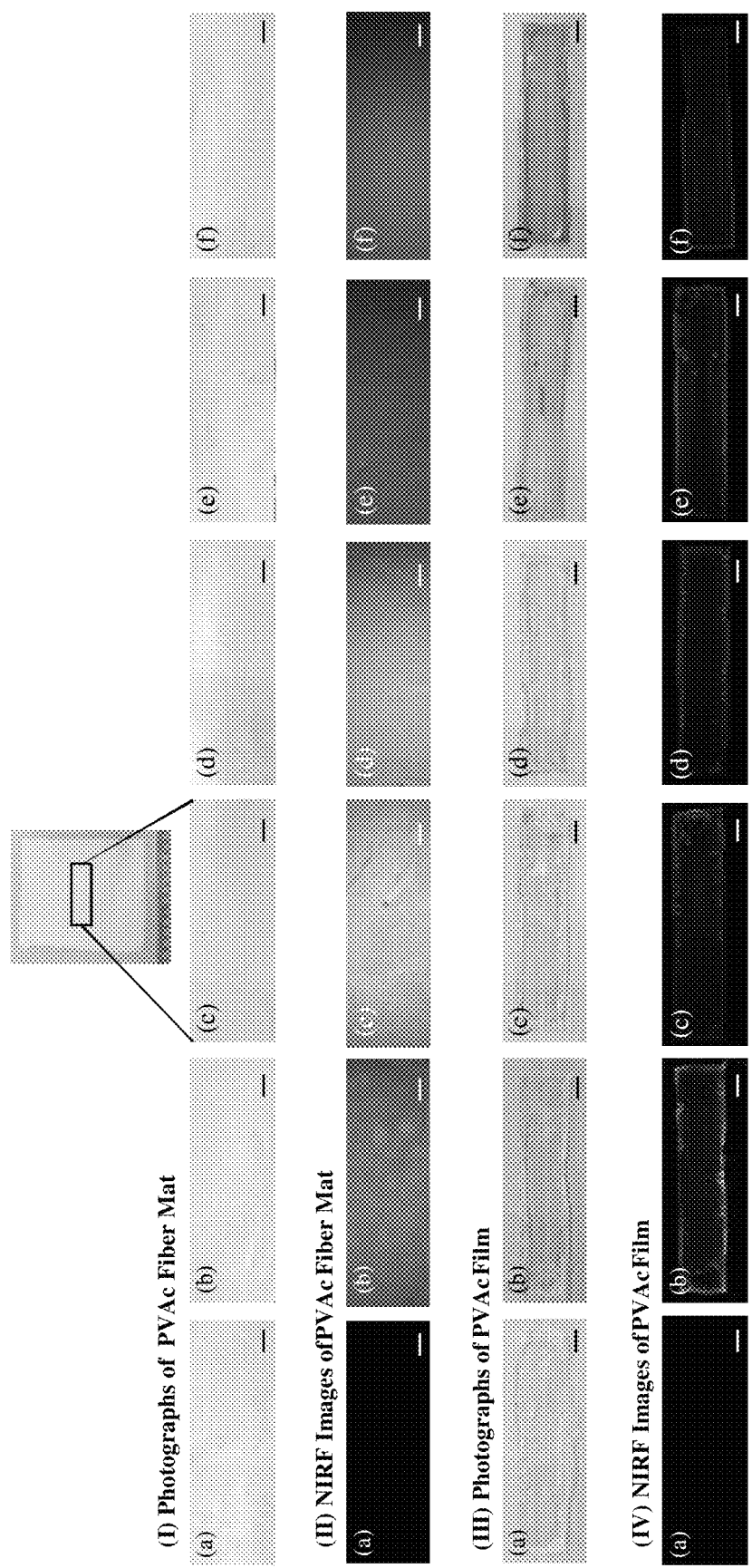

FIG. 3 is a series of images showing (I) photographs of PVAc fiber mat, (II) NIRF images of fiber mat, (III) photographs of PVAc film, (IV) NIRF images of PVAc film, each with ICG concentrations of: (a) 0 mg/ml, (b) 0.00625 mg/ml, (c) 0.0125 mg/ml, (d) 0.025 mg/ml, (e) 0.05 mg/ml, and (f) 0.125 mg/ml. The gain and exposure time were 1 and 140 ms respectively. The scale bars each represent 5 mm.

Figure 4:
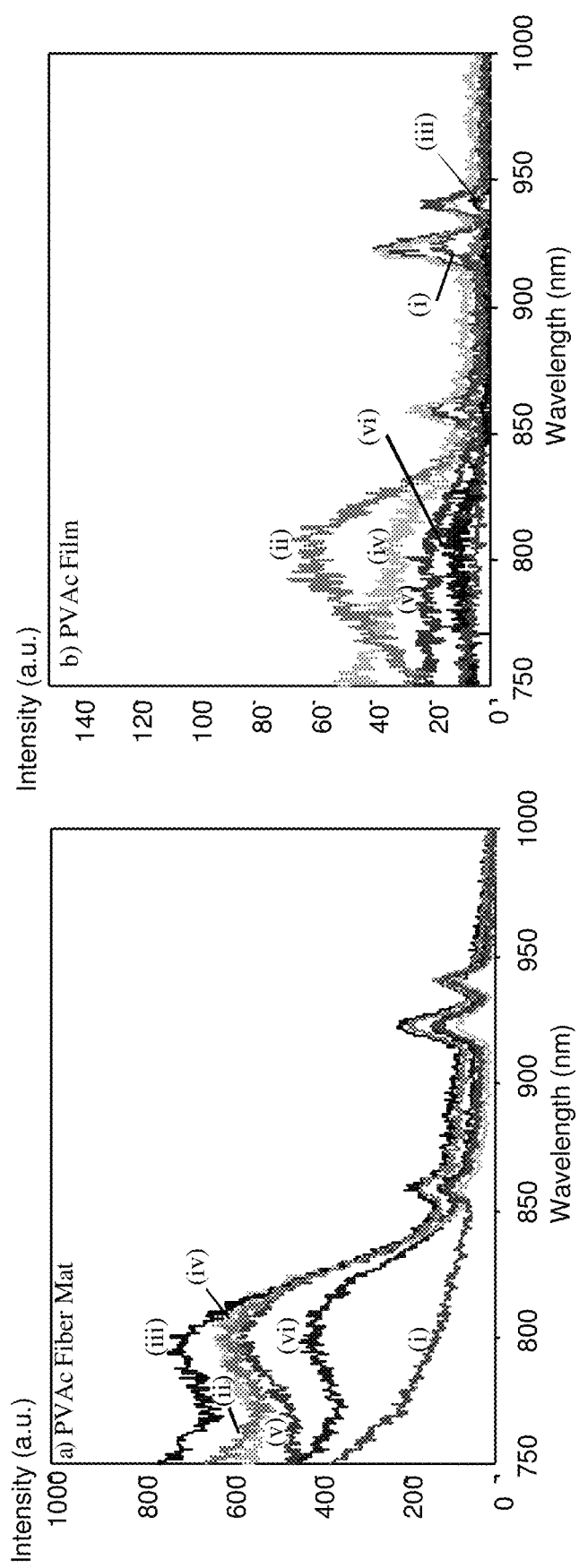

FIG. 4 is a graphical representation of spectrofluorometry of (a) PVAc fiber mat with different ICG concentration, and (b) PVAc films with ICG concentration of: (i) 0 mg/ml, (ii) 0.00625, (iii) 0.0125, (iv) 0.025, (v) 0.05, and (vi) 0.125.

Figure 5:
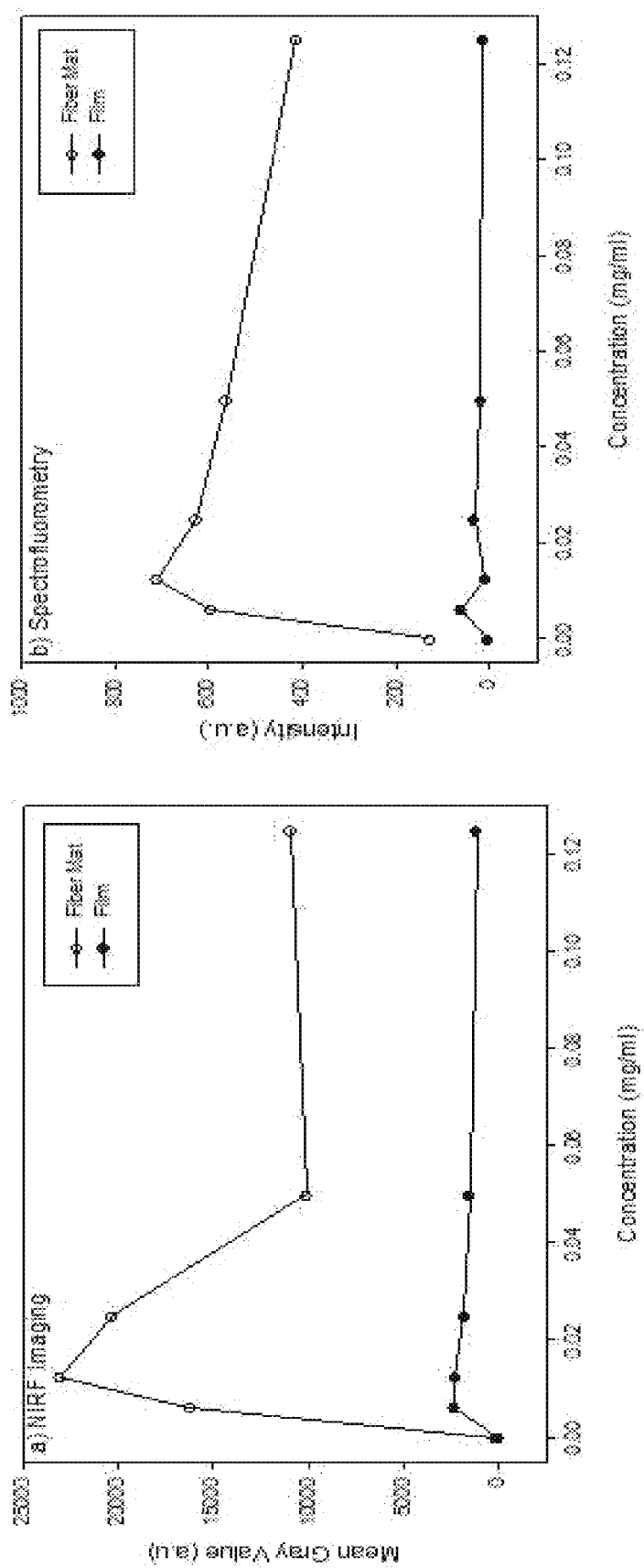

FIG. 5 is a graphical representation of a comparison of PVAc fiber mat and PVAc film with different ICG concentration by using (a) Spectrofluorometry, and (b) NIR imaging, according to an embodiment of the present invention. The mean gray values were computed by using ImageJ program. PVAc fiber mat showed higher intensity and mean gray values compared to the PVAc film. The highest intensity by spectrofluorometry and the highest mean gray value by NIR imaging were observed for samples with 0.0125 mg/ml ICG concentration.

Figure 6:
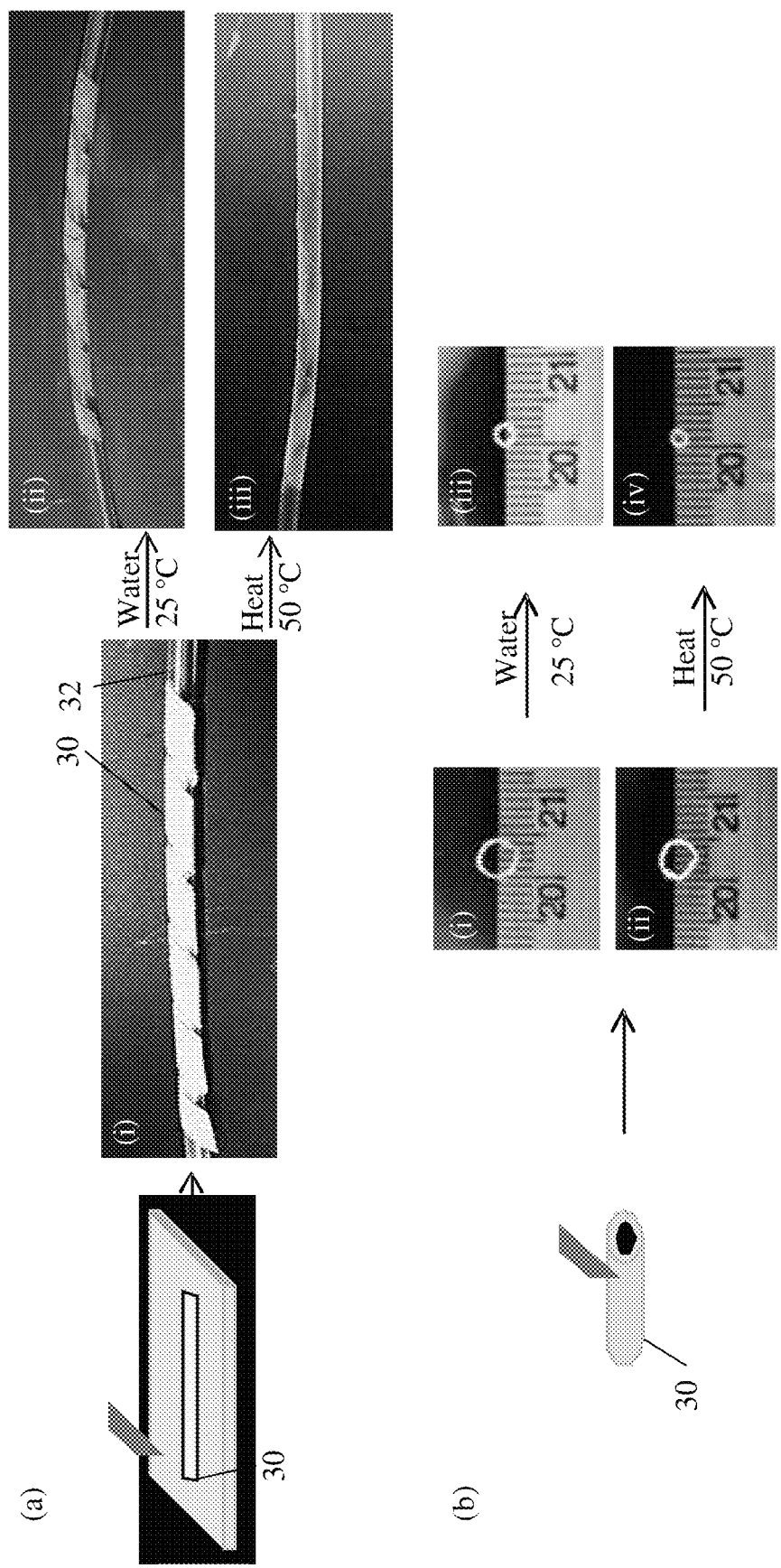

FIG. 6 is a schematic and photographic representation showing a small strip that was cut from the electrospun fiber mat and then wrapped around a pediatric catheter tube (i). The strip was shrunk on to the tube by applying (ii) 25° C. water or (iii) 50° C. heat. (b) Small rings were cut from a halo tube of electrospun fiber mat ((i) and (ii)) and recovered by applying (iii) 25° C. water and (iv) 50° C. heat.

Figure 7:
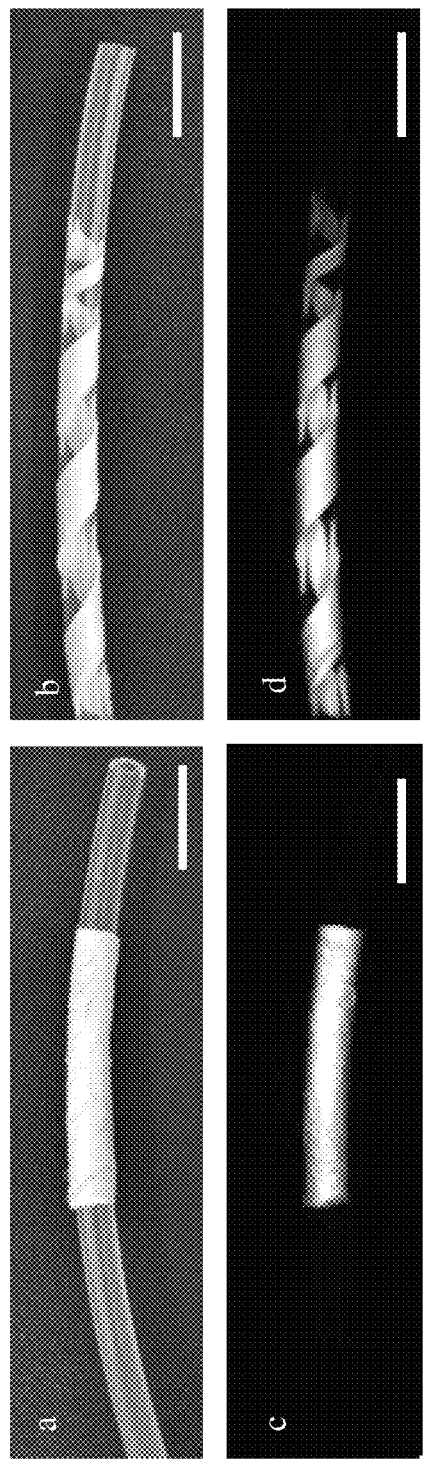

FIG. 7 is a series of images of: (a) and (b) photographs of an electrospun tube and small strip cut from electrospun fiber mat of PVAc/ICG with the ICG concentration of 0.0125 mg/ml wrapped around a pediatric catheter tube; (c) and (d) NIRF images of same devices taken with the gain of 1 and exposure time of 140 ms. The scale bar represents 10 mm.

Figure 8:
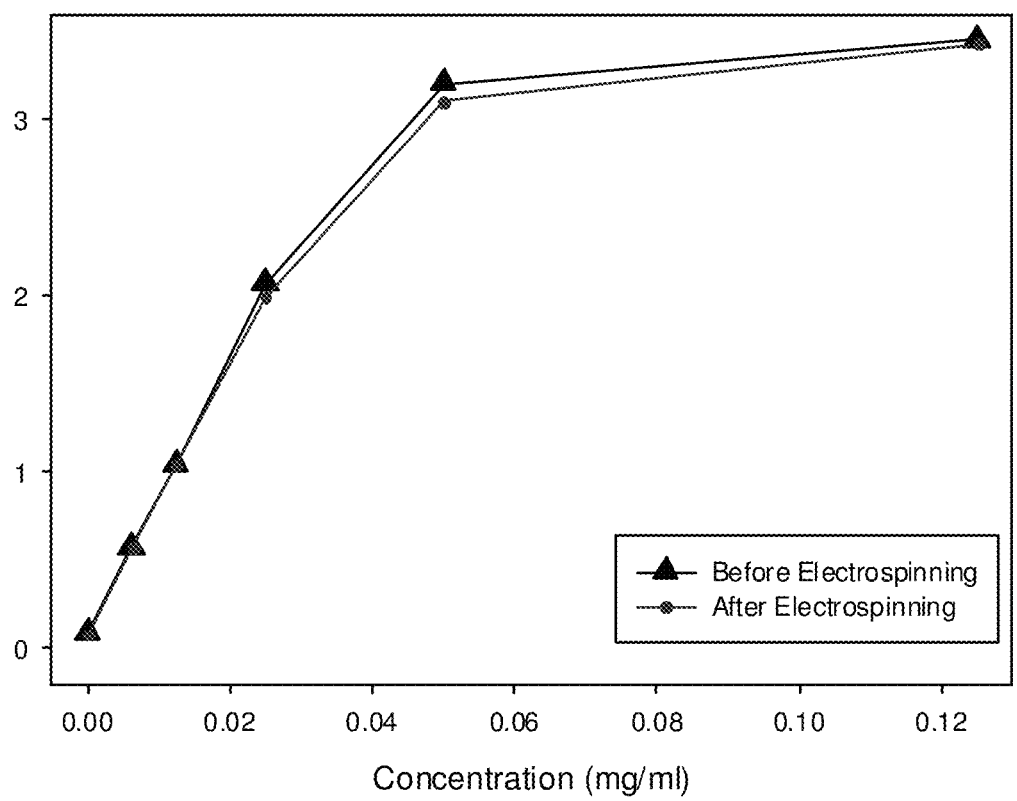

FIG. 8 is a graph of absorbance measurements using a plate reader at 790 nm for (a) polymer solutions before electropsinning and (b) after electrospinning by dissolving the fiber mats in methanol and DMF to yield the same polymer concentration.

Figure 9:
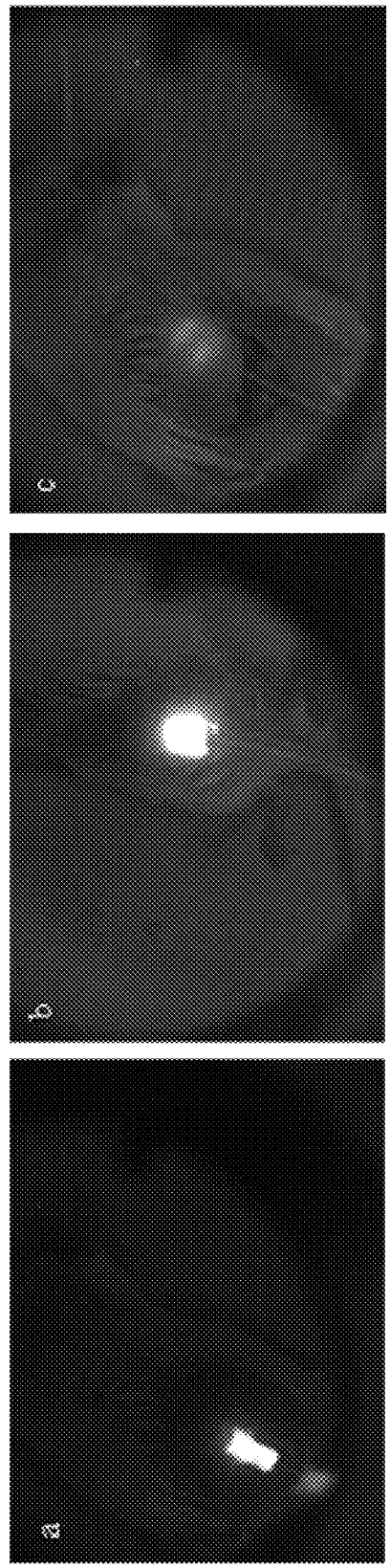

FIG. 9 is a series of NIR images of a tube coated with NIR fluorescence polymer as placed (a) subcutaneous, (b) intraperitoneal, and (c) behind the bowel in a mouse.

Figure 10:
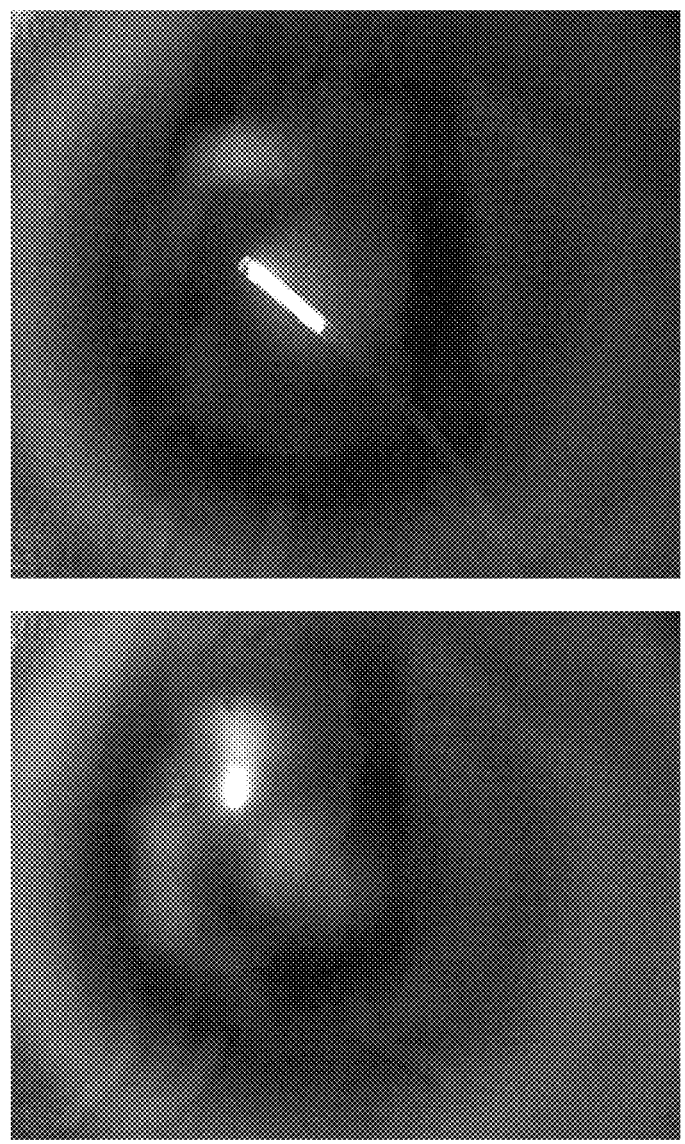

FIG. 10 is a series of NIRF images of a tube coated with NIRF polymer as placed outside and then inside a mouse.

DETAILED DESCRIPTION OF THE INVENTION

As discussed and shown herein and in the accompanying figures, a molecularly homogeneous solution of dye and polymer dissolved in a mutual solvent has been electrospun, which lead to uniform distribution of dye across the cross-section of each constituent fiber. Unexpectedly, the fluorescence intensity of dye incorporated into nanofibers is dramatically higher than when incorporated in films of the same host polymer. This effect increase in intensity is important to the successful utilization of NIR-emmitting materials in the imaging for medical devices and for other applications. Further, it was observed unexpectedly that the materials shrink dramatically upon heating. Combining the two effects allows for medical device labeling for surgical imaging with benign light rather than x-ray imaging shrink-wrap NIR bands for catheters and light-activated, subcutaneous sutures, and antimicrobial materials, for example. There are no limitations in incorporating thermally unstable dyes in this technique since the process is preferably conducted at room temperature.

Advantages of the invention are illustrated by the Examples set forth herein. However, the particular conditions and details are to be interpreted to apply broadly in the art and should not be construed to unduly restrict or limit the invention in any way.

EXAMPLE

This Example describes the preparation of a polymer solution for electrospinning, electrospinning a solution of polymer and ICG dye of varying concentrations, and the utilization of spectrofluormetry and NIR imaging to compare resulting polymer fiber mats and casted polymer films containing different concentrations of ICG dye in accordance with an embodiment of the present invention.

Figure 2A:
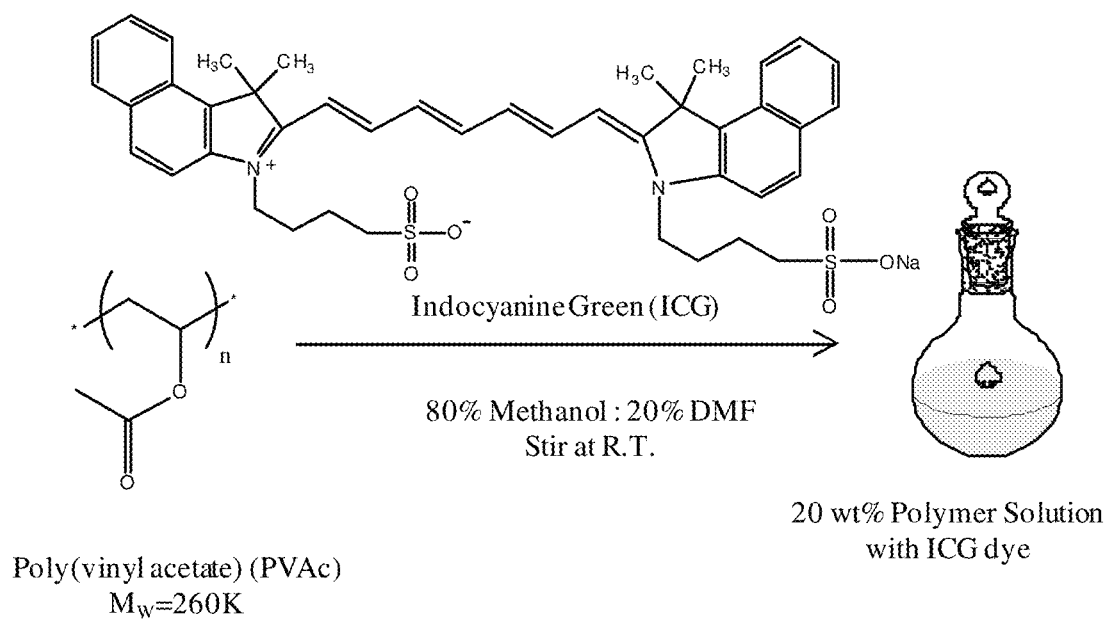
FIG. 2A is a schematic representation illustrating a procedure of incorporating ICG dye into a polymer solution according to an embodiment of the present invention.
Figure 2B:
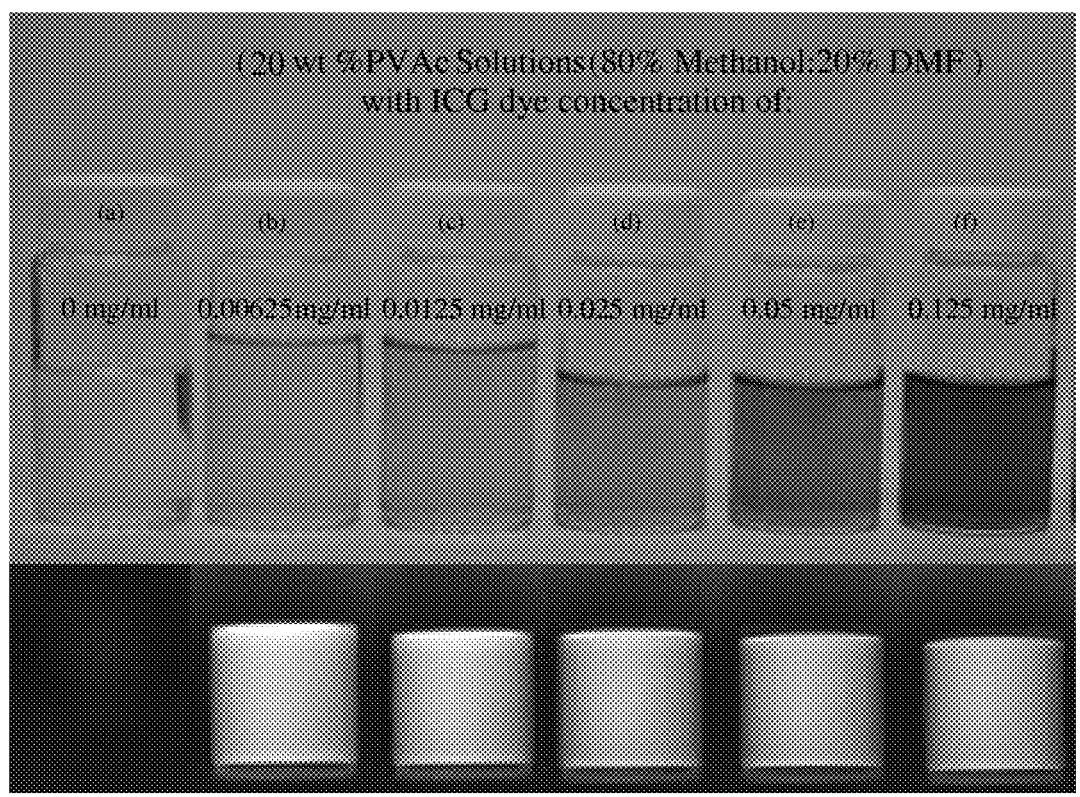
FIG. 2B is a photographic representation of ICG concentrations of (a) 0 mg/ml, (b) 0.00625 mg/ml, (c) 0.0125 mg/ml, (d) 0.025 mg/ml, (e) 0.05 mg/ml, and (f) 0.125 mg/ml along with the NIR images of the same vials under a NIRF imaging system at the gain of 1 and exposure time of 150 ms.

In a first step, the polymer solution for electrospinning can be prepared by dissolving any thermoplastic polymer in its respective solvent. Herein, poly(vinyl acetate) (PVAc) (MW=260,000 g/mole) and different concentrations of ICG were dissolved in a solution containing 80% methanol and 20% N,N-dimethylformamide (DMF) to generate a 20 wt % polymer solution as seen in FIG. 2. The electrospinning solution was then loaded into a glass syringe and electrospun using known methods to fabricate nanofibers containing the ICG dye. In this technique, uniform dye incorporation is achieved compared to incorporation of the dye via diffusion. Other shape memory polymers may be used provided that they are shrinkable as spun, i.e., they are ready to be shrunk upon electrospinning, in response to heat and/or a solvent, and will retain their fibrous nature when shrunk so that the fibrous matrix is preserved and not melted. For example, in addition to PVAc, the polymer may comprise poly(ε-caprolactone).

Figure 1A:
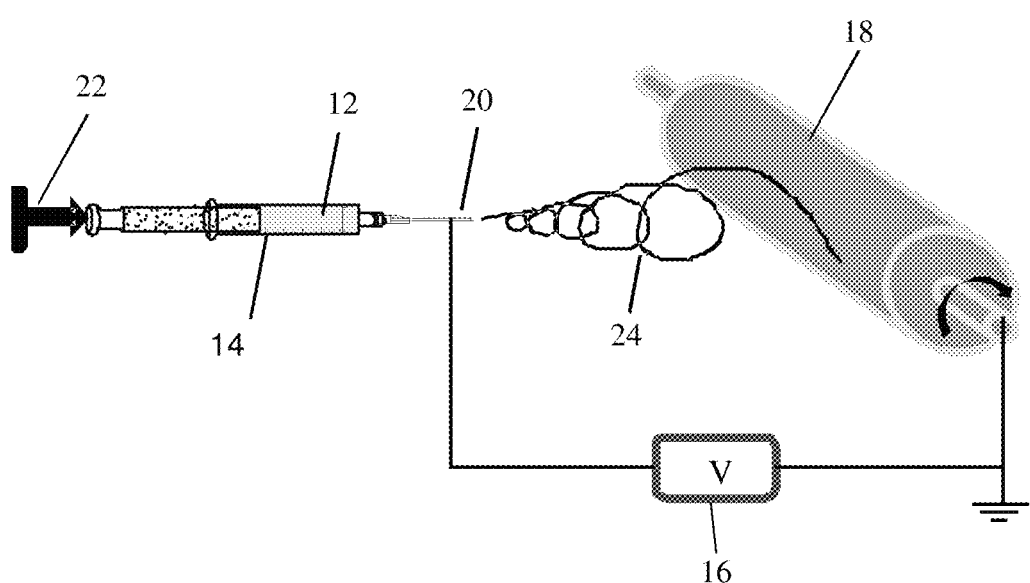
FIG. 1A is a schematic representation of an electrospinning device used in accordance with an embodiment of the present invention.
Figure 1B:
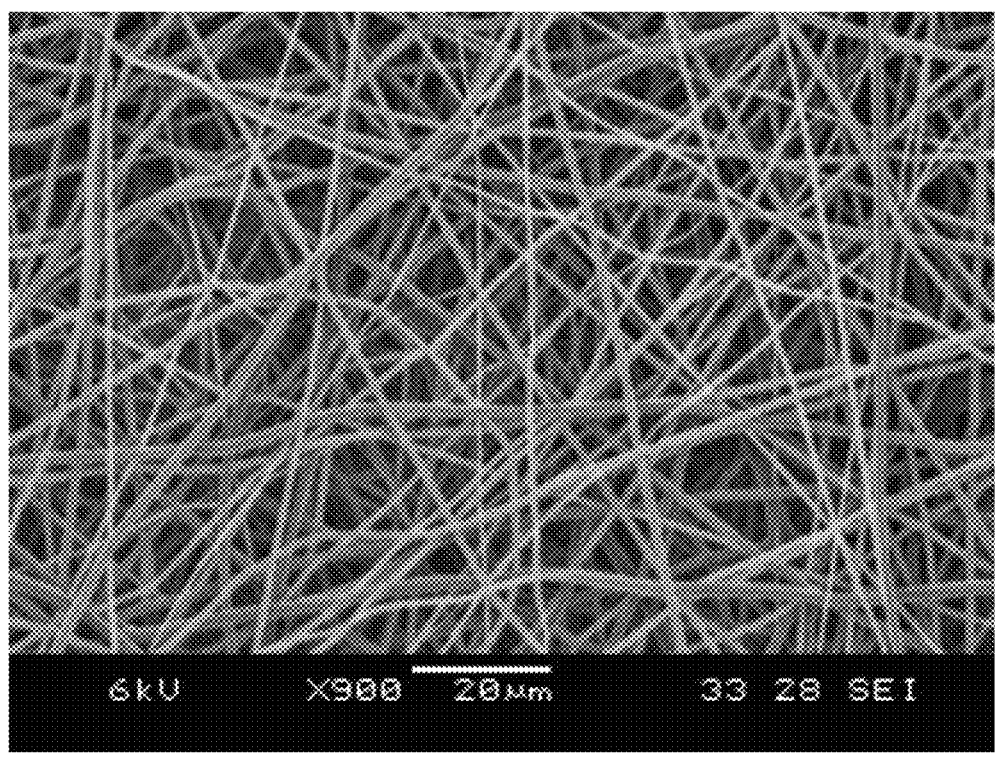
FIG. 1B is an SEM image of an electrospun fiber mat having an average fiber diameter of 0.61 µm.

FIG. 1A shows a schematic representation of an electrospinning device 10 used for this Example. For electrospinning, a polymer solution 12 is placed in a glass syringe 14 bearing a metal needle which is connected to a high voltage power supply 16. A collector 18 is grounded and rotates at the speed of 300 rpm. The electrospinning is then performed at a voltage of 8-12 kV, with 7 cm distance between the needle tip 20 and collector 18. The flow rate of the polymer solution, e.g., 1 mL per hour, is maintained by a syringe pump 22. Under the influence of the electric field, electrostatic charges build up on the surface of the liquid droplets and form a charged jet 24. Then charged jet 24 is stretched to form continuous fibers on metal collector 18. The solvent evaporates before charged jet 24 has reached collector 18. As a result, fibers are formed and collected on the surface of the metal collector 18. As seen in FIG. 1B, the electrospinning process may be used for form an electrospun fiber mat having an average fiber diameter of about 0.61 μm.

Spectrofluorometry and NIR imaging were utilized to compare polymer fiber mats and casted polymer films containing different concentration of ICG dye. FIG. 3 shows NIR imaging results of PVAc fiber mat with different ICG concentration and casted PVAc films with different ICG concentrations. Spectrofluorometry of PVAc fiber mat with different ICG concentration and casted PVAc films with different ICG concentration are shown in FIG. 4.

FIG. 5 shows graphs of comparison of PVAc fiber mat and PVAc film with different ICG concentration by using spectrofluorometry and NIR imaging as a function of concentration, noting that the mean gray values indicating intensity were computed by using ImageJ program. Unexpectedly, PVAc fiber mats showed significantly higher intensity, whether measured by spectrofluorometry or by NIR imaging, when compared to the PVAc film. Moreover, the existence of an optimum dye concentration was evident from the trends, the highest NIR emission intensities being observed for samples with 0.0125 mg/ml ICG concentration. It is understood that higher concentrations that this optimum value lead to excessive light absorption, limiting the depth to which the excitation light can penetrate the materials.

It was observed in separate experiments that PVAc fibrous webs prepared by electrospinning with the method indicated, with or without dye, exhibited significant shrinkage when heated above about 50° C. or when immersed in water, the former being faster. This surprising finding was interpreted as evidence that electrospun PVAc features frozen-in molecular orientation along the fiber axes. This molecular orientation is apparently relaxed upon heating to a temperature above Tg (glass transition temperature) or upon lowering Tg to near-room-temperature by water-plasticization.

The idea was conceived that the combination of high-intensity NIR emission and heat or water-triggered shrinkage can be combined to enable facile NIR labeling of medical devices to be imaged with NIR equipment. One application of this combination of properties is the NIR labeling of catheters via shrink-wrapping, as shown in FIG. 6, for the purpose of NIR imaging. For example, a small strip of a fiber mat 30 that has been elongated into a temporary shape is cut and then wrapped around the end of a catheter 32. Upon the application of heat, such as to 50 degrees Celsius, the fiber mat strip 30 will shrink to its permanent shame memory configuration and tighten around catheter 32 as seen in FIG. 6(a)(iii). The fiber mat may also be formed into a tube or even an end cap that can be positioned over the end of a post or other member of a medical device.

The NIR excitation and emission of ICG dye embedded in the polymer of strip 30 allows for tracking the device by using an NIR imaging system, which is non-invasive compared to other imaging techniques such as X-ray and MRI. As seen in FIG. 7, excitation of strip 30 with the appropriate infrared wavelength results in near infrared emissions that are easy to capture using a near infrared filter and camera.

Referring to FIG. 8, testing of near infrared emissions prior to and after electrospinning establishes that the ICG is responsible for post-electrospinning fluorescence.

As seen in FIG. 9, positioning of a near infrared marker comprising a NIR fluorescence polymer according to the present invention allows for visualization of the catheter when it is inserted into a patient (in this case a mouse). The marked catheter is visible when placed subcutaneously, intraperitoneally, and even behind the bowel. As further seen in FIG. 10, a tube coated with an NIRF polymer according to the present invention is readily visualized when the marked tube is placed outside and then inside a mouse.

Another application of the present invention is light-activated shape memory PVAc fiber mat containing ICG that will shrink in response to light activation for easy positioning on a medical device. For example, light-activated shape change through photo-thermal heating of the materials with relatively high intensity NIR-excitation is possible. Using higher intensity incident NIR light than is used for imaging, the materials are expected to heat up and once the temperature exceeds Tg they will shrink, bend, twist, or contract, depending on configuration. A surgical application envisioned for such a light-activated SMP is internal suturing, where the suture itself can be located by NIR imaging and then activated (partially or completely) from outside the body by using NIR irradiation. This will tighten the loosened sutures without the need for an open incision. Periodic and continued contraction of subcutaneous sutures may be useful for plastic surgery.

Other potential applications of the PVAc fiber mat with incorporated ICG include antimicrobial medical devices, packaging, drug delivery, and temperature sensors.

Although the present invention has been described in connection with a preferred embodiment, it should be understood that modifications, alterations, and additions can be made to the invention without departing from the scope of the invention as defined by the claims.

What is claimed is:

1. A near infrared fluorescent marker for a target medical device, comprising:
   a fiber mat including a plurality of fibers formed from a shape memory polymer and a near infrared dye that is homogenously distributed within the plurality of fibers of said shape memory polymer;
   wherein the shape memory polymer is programmed to shrink from a temporary shape to a permanent shape in response to a stimulus so that said fiber mat will shrink around a portion of the target medical device; and
   wherein said near infrared dye within the plurality of fibers of fiber mat will emit fluorescence between 750 nm and 950 nm when subject to near infrared excitation after the fiber mat has been shrunk around the portion of the target medical device.

2. The marker of claim 1, wherein said polymer and said dye are present in a ratio of 0.00625 milligrams to 1.25 milligrams of dye per 2.0 grams of polymer.

3. The marker of claim 1, wherein said shape memory polymer has a transition temperature below 50 degrees Celsius.

4. The marker of claim 3, wherein said shape memory polymer is poly(vinyl acetate).

5. The marker of claim 4, wherein said dye is indocyanine green.

6. The marker of claim 4, wherein said dye has an excitation wavelength and an emission wavelength in the near infrared spectrum.

7. A method of visualizing a medical device positioned in a patient, comprising the steps of:
- providing a near infrared marker comprising a fiber mat including a plurality of fibers formed from a shape memory polymer and a near infrared dye that is molecularly homogenously distributed within the plurality of fibers of said shape memory polymer, wherein the shape memory polymer is programmed to shrink from a temporary shape to a permanent shape in response to a stimulus so that said fiber mat will shrink around a portion of a target medical device and wherein said near infrared dye will emit fluorescence between 750 nm and 950 nm when subject to near infrared excitation after the fiber mat has been shrunk around the portion of the target medical device;
- positioning the near infrared marker around a portion of said target medical device;
- stimulating the shape memory polymer of the near infrared marker so that the fiber mat shrinks from the temporary shape to the permanent shape;
- positioning said target medical device and said near infrared marker within said patient;
- exciting said near infrared marker with near infrared light so that the near infrared marker fluoresces between 750 nm and 950 nm;
- capturing any near infrared emissions from said near infrared marker and from a predetermined area of said patient proximate to said near infrared marker; and
- displaying said near infrared emissions from said near infrared marker and said proximate area.

8. The method of claim 7, wherein the temporary shape of said near infrared marker is configured into a tube.

9. The method of claim 8, wherein the step of positioning the near infrared marker around a portion of said target medical device comprises the step of positioning said target medical device in said tube and the step of stimulating the near infrared marker comprises the step of applying heat until said tube constricts around said target medical device.

10. The method of claim 7, wherein said near infrared marker is configured into a strip.

11. The method of claim 7, wherein said near infrared marker is configured into an end cap.

12. The method of claim 9, wherein said shape memory polymer comprises poly(vinyl acetate).

13. The method of claim 10, wherein said dye comprises indocyanine green.

14. The marker of claim 1, wherein said near infrared dye of said electrospun fibrous web has a highest near infrared (NIR) emission intensity at a concentration of 0.0125 milligrams of said dye per 2.0 grams of said polymer.

* * * * *